United States Patent [19]

Saunders

[11] 4,106,910

[45] Aug. 15, 1978

[54] RAS-GAS DILUTION DEVICE

[75] Inventor: Raymond A. Saunders, Hyattsville, Md.

[73] Assignee: The United States of America as represented by the Secretary of the Navy, Washington, D.C.

[21] Appl. No.: 825,351

[22] Filed: Aug. 16, 1977

[51] Int. Cl.² .................... G01N 1/22; G01N 1/26
[52] U.S. Cl. ................. 23/232 R; 23/254 R; 73/421.5 R
[58] Field of Search ............ 23/232 R, 232 E, 254 R, 23/254 E; 73/421.5

[56] References Cited

U.S. PATENT DOCUMENTS

| 3,461,727 | 8/1969 | Everhard et al. | 73/421.5 R |
| 3,485,015 | 12/1969 | Vecchio | 23/254 R |
| 3,641,821 | 2/1972 | Neuberger et al. | 23/254 R |
| 3,690,837 | 9/1972 | Witz et al. | 23/232 R |
| 3,699,814 | 10/1972 | Kaufman | 73/421.5 R |

Primary Examiner—R.E. Serwin
Attorney, Agent, or Firm—R. S. Sciascia; Philip Schneider; Melvin L. Crane

[57] ABSTRACT

A method and device for diluting a first gas mixture having a known concentration of a given gas to obtain a second gas mixture containing a lower known concentration of the given gas. The device enables one to mix gases with appropriately low concentrations of a particular gas such that the gaseous mixture may be used to calibrate an instrument that measures such low concentrations of a gas.

9 Claims, 1 Drawing Figure

U.S. Patent    Aug. 15, 1978    4,106,910
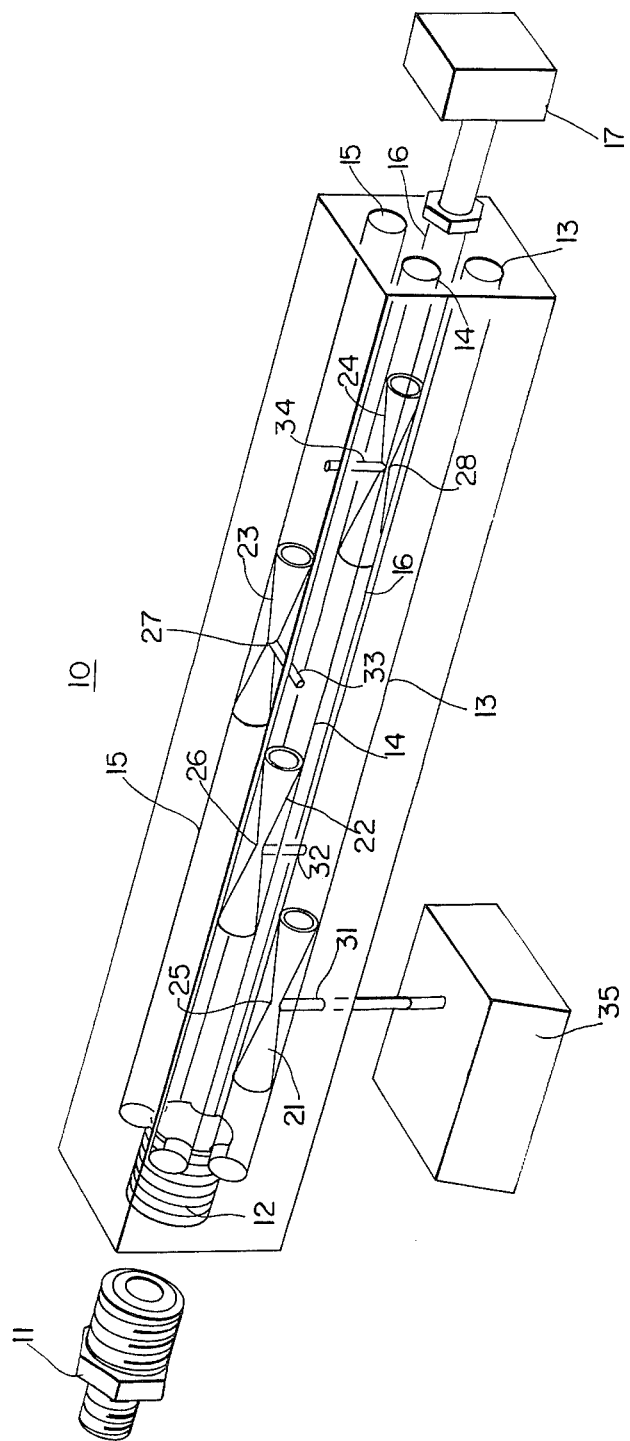

RAS-GAS DILUTION DEVICE

BACKGROUND OF THE INVENTION

This invention relates to fluid mixtures and more particularly to a method and device for mixing fluids to obtain a known concentration whereby instrumentation for measuring fluid concentrations may be calibrated.

Present day concern for the quality of environmental atmospheres requires accurate sophisticated analytical instrumentation for the detection and monitoring of specific contaminants. This is especially true in confined areas such as those of a submarine, diving habitats, spacecraft, or other such confined areas. Proposed requirements of atmospheric contaminant measurements have extended in some instances beyond the capability of current measuring instrumentation. Therefore new analytical concepts and instrumentation must be developed to cope with the present needs. One major problem exists, however, in that instrumentation cannot be evaluated for accuracy and low concentrations of gases unless there is a suitable instrument to accurately form the low concentrations desired for calibration.

A conventional method of producing a dynamic gas stream containing a very low concentration of another gaseous substance involves a series of successive blendings of separate gas streams at different flow rates. Several stages may be required and the flow rate of each stage of dilution must be accurately controlled. This method is not satisfactory where very low concentrations (parts per billion or less) are required, because of the difficulty of adjusting and maintaining accurate gas flows. In this type of prior art, an adjustment or change in flow rate at any one stage upsets the flow rate at all other stages. Further, such instruments are large, fragile and contain considerable interconnecting tubing.

SUMMARY OF THE INVENTION

This invention makes use of a gas flow input, common to a plurality of successive stages, that feeds each stage with equal gas flow. Each stage is provided with a venturi jet with its low-pressure point working into the downstream leg of the preceeding venturi. Each venturi is made with the same size orifice of any desired ratio to provide a desired gas flow between the diluting gas through-put stream and the gas to be diluted flowing through the side or low-pressure port into the flowing stream.

BRIEF DESCRIPTION OF THE DRAWING

The drawing illustrates a perspective view of the device.

DETAILED DESCRIPTION

In carrying out the method of the invention, a relatively small device may be used such as a 1-inch square of Teflon 6 inches in length. As shown, the device 10 is provided with an inlet connector 11 which connects with inlet 12. Inlet 12 provides a common feed of equal gas pressure and flow to each of four passages 13-16 of equal diameter that extend the length of the device from the inlet. Three of the passages are open to the outside and one passage connects with an instrument 17 to be calibrated or to any other desired element.

Each of the passages is provided with an identical venturi jet 21-24 each of which includes an orifice, or low-pressure port, 25-28, at the point of smallest area in the Venturi jet. The Venturi jets are placed successively downstream from the inlet port and form first, second, third, and fourth stages. The fourth stage is in the passage 16 that connects with the instrument to be calibrated. The orifice in the venturi may be made of any desired set size which will provide any desired ratio of flow between the throughput diluting gas stream and the gas to be diluted flowing through the low-pressure port and low-pressure arm, or tube 31 which extends from the first stage into a chamber 35 that contains the gas to be diluted. The low-pressure arm, or tube 32 of the second stage venturi 22 taps into the first passage 13 downstream of its venturi 21; the tube 33 of the third-stage venturi 23 taps into the second passage 14 downstream of its venturi 22; and so on. The first stage is the passage that contains the Venturi closest to the inlet port. The low-pressure port is compatible with the orifice in the Venturi so that the gas flow in the passage will be a set ratio with respect to the flow of gas through the low-pressure port into the main stream of that particular passage. For example, a ratio of 100 to 1 or 1,000 to 1 may be made. If there are four stages, as shown, of 100:1 dilution ratio, the overall dilution of the initial gas will be $10^8$.

As an example of operation, assume that air containing 200,000 parts per million (ppm) of oxygen is contained in the chamber 35 and the gas input through input 12 is helium gas. At the first stage, the air and oxygen will be drawn into the main gas stream and mixed with the helium. The output of the first stage will be helium and air containing 2,000 ppm of oxygen. Downstream of the first stage, the second stage will draw a portion of the helium-air-oxygen mixture into the main stream of the second stage. Since the ratio is 100 to 1, the amount of oxygen in the second stream will be 20 ppm. The third stage is downstream of the second stage and the main stream through the third stage will be diluted to 0.20 ppm of oxygen. The fourth and final stage is downstream of the third stage and the fourth stream will be diluted to contain 2 pp billion of oxygen.

Since the flow ratio may be made with a ratio of 1000 to 1, it is seen that with a four-stage device the parts-ratio, could be lowered considerably; i.e., down to $<1$ pp trillion. Further, the device may be made with more than four stages which will further reduce the ratio of the parts in the output of the final stage.

The device such as illustrated may be made of a 1 inch $\times$ 1 inch $\times$ 6 inch block of Teflon including $\frac{1}{4}$-inch passages that extend from the output end to the inlet. The gas flow in the inlet is equally distributed to each of the four passages and the gas flow in each passage passes through the venturi in its passage. The low-pressure port has a diameter chosen to provide the desired split ratio and is provided with a tube that extends to its gas-flow feed. The first stage has a tube that extends into the chamber containing the gas to be diluted and the tubes from each of the other stages extends into the outlet portion of the preceeding stages in consecutive order of their stage numbers. The outlet of the final stage is connected to the inlet of an instrument or other device to be calibrated, or to any desired element.

Each of the outlets of each stage may also be connected with a separate instrument to provide the gas concentration of that particular outlet if so desired.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. A device for diluting a fluid flow to a desired diluted concentration of a desired fluid which comprises:

a plurality of fluid flow passages each of equal diameter and extending parallel with each other, an inlet communicating with one end of each of said passages for distributing a fluid of equal flow ratio through each of said passages, an outlet communicating with each of said passages at their ends opposite said inlet, a venturi in each of said passages with each venturi equally spaced from each other along the axial length, a low-pressure tube communicating with the venturi positioned close to said inlet for feeding a fluid to be diluted into said venturi for dilution by fluid flow through said passage containing said venturi, a separate, low-pressure tube communicating with each venturi downstream of said venturi closest said inlet, with one each of said separate low-pressure tubes extending from the passage containing the preceding venturi to the venturi immediately downstream of the venturi in the passage from which the low-pressure tube extends, whereby each succeeding venturi axially downstream from said venturi closest said inlet further dilutes the fluid to be diluted in order of their axial placement subsequent to being fed into said venturi closest said inlet.

2. A device as claimed in claim 1 which includes first and second passages, whereby the tube communicating with said venturi in said first passage feeds a gas into said venturi in said first passage for dilution by gas flowing therethrough from said inlet, and the tube communicating with the venturi in said second passage communicates with said first passage downstream of said venturi therein to feed a gas flow from said first passage into said second passage for dilution by the gas flow through said second passage.

3. A device as claimed in claim 2 which includes third and fourth passages, said venturi in said third passage communicating with said second passage downstream of said venturi therein, and said venturi in said fourth passage communicating with said third passage downstream of said venturi in said third passage, whereby the gas flow drawn into said third and fourth passages are each further diluted respectively by the gas flow in each respective passage.

4. A method of diluting a gas flow to a desired concentration containing a dilutant gas which comprises:

directing a gas flow of the diluting gas into at least two equal size passages extending along the length of a housing with the gas flow evenly distributed into each of said passages and with the same gas flow rate, directing the gas flow in each passage through a venturi in each of said passages wherein each venturi forms a gas diluting stage with each of said gas diluting stages placed in successive order along the length of said housing with the low pressure port of each successive stage communicating with the gas flow passage downstream of the venturi in the preceeding stage with the low pressure port of the first stage communicating with a chamber containing the gas to be diluted, feeding a gas to be diluted at a controlled rate into the gas flowing through said first stage in said passage, feeding the gaseous mixture in said first passage downstream of said first stage into the second stage to mix with said gas flowing through said venturi in said second passage to further dilute the gaseous flow from said first passage to said second passage, and directing the diluted gas from the downstream passage of the second venturi into the next passage and likewise to as many passages as there are passages.

5. A method as claimed in claim 4 in which, there are four passages each of which include a venturi whose low pressure side communicates with the downstream output of the previous positioned venturi to feed a gaseous mixture into the next succeeding passage for dilution by the gas flow in that passage.

6. A fluid dilution device comprising:

first connection means for connection to a first supply means for providing a first fluid at a constant rate of flow;

a plurality of unconnected passages, each individually coupled to said first connection means;

a plurality of Venturi tubes, each having a low-pressure arm connected through a low-pressure port to the point of smallest cross-sectional area in a Venturi jet, and each Venturi-jet being located within a different one of said passages with its low-pressure arm extending outside the passage, the ratio of flow of fluid through the low-pressure port to flow of fluid in the Venturi jet being known for each Venturi tube; and second connection means for connecting to a second supply means for providing a mixture of fluids with the concentration of one of said fluids in the mixture being a known value, the low-pressure arm of a first of said Venturi tubes being connected to said second connection means, the low-pressure arm of a second of said Venturi tubes being connected downstream of the Venturi tube in the passage in which said first Venturi tube is located, and all other low-pressure arms being similarly connected in sequence to different passages downstream of their associated Venturi tubes, so that the concentration of said one of said fluids at the output of each passage is a known value and is a lower value for each passage in sequence.

7. A device as in claim 6 further including a housing for containing said first connection means, said passages and said Venturi jets.

8. A device as in claim 6, where all said fluids are gases.

9. A device as in claim 6, where all ratios of flow of fluid through the low-pressure port to flow in the Venturi jet are the same.

* * * * *